(12) United States Patent
Frijlink et al.

(10) Patent No.: US 7,967,753 B2
(45) Date of Patent: Jun. 28, 2011

(54) PULSE INVERSION SEQUENCES FOR NONLINEAR IMAGING

(75) Inventors: Martijn Egbert Frijlink, Rotterdam (NL); David Eric Goertz, Rotterdam (NL); Antonius Franciscus Wilhelmus van der Steen, Rotterdam (NL)

(73) Assignee: Stichting Voor de Technische Wetenschappen of Van Vollenhovenlaan, Utrecht (NL)

( * ) Notice: Subject to any disclaimer, the term of this patent is extended or adjusted under 35 U.S.C. 154(b) by 949 days.

(21) Appl. No.: 11/832,457

(22) Filed: Aug. 1, 2007

(65) Prior Publication Data
US 2008/0077018 A1    Mar. 27, 2008

Related U.S. Application Data

(60) Provisional application No. 60/821,106, filed on Aug. 1, 2006, provisional application No. 60/824,862, filed on Sep. 7, 2006.

(51) Int. Cl.
*A61B 8/00* (2006.01)
*A61B 8/14* (2006.01)

(52) U.S. Cl. .................. 600/443; 600/458; 600/462

(58) Field of Classification Search .................. None
See application file for complete search history.

(56) References Cited

U.S. PATENT DOCUMENTS

| | | |
|---|---|---|
| 3,778,756 A | 12/1973 | Houston et al. |
| 5,186,177 A | 2/1993 | O'Donnell et al. |
| 5,269,307 A | 12/1993 | Fife et al. |
| 5,271,928 A | 12/1993 | Schneider et al. |
| 5,410,516 A | 4/1995 | Uhlendorf et al. |
| 5,413,774 A | 5/1995 | Schneider et al. |
| 5,445,813 A | 8/1995 | Schneider et al. |
| 5,523,058 A | 6/1996 | Umemura et al. |
| 5,597,549 A | 1/1997 | Schneider et al. |
| 5,632,277 A * | 5/1997 | Chapman et al. ............. 600/443 |
| 5,678,553 A | 10/1997 | Uhlendorf et al. |
| 5,696,737 A | 12/1997 | Hossack et al. |
| 5,706,819 A * | 1/1998 | Hwang et al. ................. 600/458 |
| 5,771,933 A | 6/1998 | Akamatsu et al. |
| 5,793,701 A | 8/1998 | Wright et al. |
| 5,827,504 A | 10/1998 | Yan et al. |
| 5,833,613 A | 11/1998 | Averkiou et al. |

(Continued)

FOREIGN PATENT DOCUMENTS
EP       0014793       9/1980
(Continued)

OTHER PUBLICATIONS

Bouakaz, A., IEEE Trans Ultrason Ferroelec Freq Control, vol. 50 No. 5 (2003) pp. 496-506.

(Continued)

*Primary Examiner* — Long V Le
*Assistant Examiner* — Angela M Hoffa
(74) *Attorney, Agent, or Firm* — Frommer Lawrence & Haug LLP; Bruce E. Black

(57) ABSTRACT

Provided herein are Pulse-Inversion (PI) sequences that provide for fundamental frequency suppression in nonlinear imaging applications. In an embodiment, a weighting scheme is applied to the received echo pulses resulting from transmit pulses of alternating polarity to reduce the effect of transducer motion. In an embodiment, a three-pulse weighting scheme is applied to a PI sequence. In other embodiments, different combinations of the three-pulse weighting scheme are applied to a PI sequence.

50 Claims, 3 Drawing Sheets

U.S. PATENT DOCUMENTS

| | | | |
|---|---|---|---|
| 5,833,615 A | 11/1998 | Wu et al. | |
| 5,865,751 A | 2/1999 | Okuno et al. | |
| 5,879,303 A | 3/1999 | Averkiou et al. | |
| 5,891,038 A | 4/1999 | Seyed-Bolorforosh et al. | |
| 5,902,243 A | 5/1999 | Holley et al. | |
| 5,908,389 A | 6/1999 | Roundhill et al. | |
| 5,919,137 A | 7/1999 | Finger et al. | |
| 5,980,459 A | 11/1999 | Chiao et al. | |
| 6,015,385 A | 1/2000 | Finger et al. | |
| 6,050,942 A | 4/2000 | Rust et al. | |
| 6,064,628 A | 5/2000 | Uhlendorf et al. | |
| 6,074,348 A | 6/2000 | Chiao et al. | |
| 6,095,980 A | 8/2000 | Burns et al. | |
| 6,108,572 A | 8/2000 | Panda et al. | |
| 6,117,082 A | 9/2000 | Bradley et al. | |
| 6,120,448 A | 9/2000 | Bradley et al. | |
| 6,139,501 A | 10/2000 | Roundhill et al. | |
| 6,155,981 A * | 12/2000 | Ermert et al. | 600/453 |
| 6,171,246 B1 | 1/2001 | Averkiou et al. | |
| 6,179,781 B1 | 1/2001 | Phillips | |
| 6,186,949 B1 | 2/2001 | Hatfield et al. | |
| 6,186,950 B1 * | 2/2001 | Averkiou et al. | 600/443 |
| 6,190,322 B1 | 2/2001 | Clark | |
| 6,193,662 B1 | 2/2001 | Hwang | |
| 6,193,663 B1 | 2/2001 | Napolitano et al. | |
| 6,210,332 B1 | 4/2001 | Chiao et al. | |
| 6,210,334 B1 | 4/2001 | Phillips | |
| 6,221,018 B1 | 4/2001 | Ramamurthy et al. | |
| 6,228,031 B1 | 5/2001 | Hwang et al. | |
| 6,241,674 B1 | 6/2001 | Phillips et al. | |
| 6,251,074 B1 | 6/2001 | Averkiou et al. | |
| 6,283,919 B1 | 9/2001 | Roundhill et al. | |
| 6,287,258 B1 | 9/2001 | Phillips | |
| 6,302,845 B2 * | 10/2001 | Shi et al. | 600/438 |
| 6,312,386 B1 | 11/2001 | Bolorforosh et al. | |
| 6,315,729 B1 | 11/2001 | Averkiou et al. | |
| 6,319,203 B1 | 11/2001 | Averkiou | |
| 6,333,021 B1 | 12/2001 | Schneider et al. | |
| 6,358,210 B2 | 3/2002 | Gee et al. | |
| 6,436,041 B1 * | 8/2002 | Phillips et al. | 600/437 |
| 6,436,046 B1 | 8/2002 | Napolitano et al. | |
| 6,454,714 B1 | 9/2002 | Ng et al. | |
| 6,497,665 B1 * | 12/2002 | Hunt et al. | 600/458 |
| 6,511,426 B1 | 1/2003 | Hossack et al. | |
| 6,537,222 B1 | 3/2003 | Clark et al. | |
| 6,540,684 B2 | 4/2003 | Averkiou et al. | |
| 6,544,182 B2 | 4/2003 | Averkiou | |
| 6,575,910 B2 | 6/2003 | Averkiou et al. | |
| 6,602,195 B1 | 8/2003 | Krishnan | |
| 6,605,043 B1 | 8/2003 | Dreschel et al. | |
| 6,607,490 B2 | 8/2003 | Ogasawara et al. | |
| 6,645,147 B1 | 11/2003 | Jackson et al. | |
| 6,652,463 B2 * | 11/2003 | Hunt et al. | 600/458 |
| 6,666,824 B2 | 12/2003 | Rust et al. | |
| 6,749,569 B1 | 6/2004 | Pellegretti | |
| 6,755,787 B2 | 6/2004 | Hossack et al. | |
| 6,773,401 B1 | 8/2004 | Dreschel et al. | |
| 6,786,097 B2 | 9/2004 | Song et al. | |
| 6,827,685 B2 | 12/2004 | Lin et al. | |
| 6,909,796 B2 | 6/2005 | Pomata et al. | |
| 6,969,353 B2 * | 11/2005 | Brock-Fisher et al. | 600/458 |
| 7,094,204 B2 | 8/2006 | Banjanin et al. | |
| 7,591,788 B2 * | 9/2009 | Phillips et al. | 600/458 |
| 7,666,139 B2 * | 2/2010 | Kakee et al. | 600/443 |
| 7,713,209 B2 * | 5/2010 | Guracar | 600/458 |
| 2002/0040189 A1 | 4/2002 | Averkiou et al. | |
| 2002/0042576 A1 | 4/2002 | Averkiou | |
| 2002/0055681 A1 | 5/2002 | Averkiou et al. | |
| 2003/0018253 A1 | 1/2003 | Napolitano et al. | |
| 2003/0036704 A1 | 2/2003 | Cerofolini | |
| 2003/0069504 A1 | 4/2003 | Wilkening et al. | |
| 2003/0073907 A1 | 4/2003 | Taylor | |
| 2004/0034305 A1 | 2/2004 | Song et al. | |
| 2004/0059218 A1 | 3/2004 | Kanda et al. | |
| 2004/0087857 A1 | 5/2004 | Napolitano et al. | |
| 2004/0133106 A1 | 7/2004 | Kakee et al. | |
| 2004/0230121 A1 | 11/2004 | Hansen et al. | |
| 2004/0254462 A1 | 12/2004 | Kawagishi et al. | |
| 2005/0033167 A1 | 2/2005 | Trucco et al. | |
| 2005/0049496 A1 | 3/2005 | Guracar | |
| 2005/0124882 A1 | 6/2005 | Ladabaum et al. | |
| 2006/0084874 A1 | 4/2006 | Imamura et al. | |
| 2008/0051660 A1 * | 2/2008 | Kakadaris et al. | 600/454 |

FOREIGN PATENT DOCUMENTS

| | | |
|---|---|---|
| EP | 0619104 | 10/1994 |
| EP | 1004894 | 5/2000 |
| GB | 2434449 | 7/2007 |
| JP | 2213332 | 8/1990 |
| JP | 2000005163 | 1/2000 |
| JP | 2001314499 | 11/2001 |
| JP | 2002238900 | 8/2002 |
| JP | 2002369817 | 12/2002 |
| WO | WO 97/29783 | 8/1997 |
| WO | WO 00/49427 A | 8/2000 |
| WO | WO 02/17296 A | 2/2002 |
| WO | WO 94/06380 | 9/2003 |
| WO | WO 2004/069284 | 8/2004 |
| WO | WO 2005/071437 | 8/2005 |
| WO | WO 2005/074365 | 8/2005 |
| WO | WO 2005/107600 | 11/2005 |
| WO | WO 2006/001697 | 1/2006 |
| WO | WO 2006/015876 | 2/2006 |
| WO | WO 2006/015877 | 2/2006 |
| WO | WO 2006/105877 | 2/2006 |
| WO | WO 2006/021400 | 3/2006 |

OTHER PUBLICATIONS

Frijlink, M.E., J Acoustic Soc Am, vol. 120 No. 3 (2006).

Goertz, D. E., Ultrasound in Med & Biol, vol. 32 No. 4 (2006) pp. 491-502.

Shen, C. C., IEEE Trans Ultrason Ferroelec Freq Control, vol. 50 No. 9 (2003) pp. 1124-1133.

Simpson, D. H. H., IEEE Trans Ultrason Ferroelec Freq Control, vol. 46 No. 2 (1999) pp. 372-382.

Vos, H. J., Abstract of the Eleventh European Symposium on Ultrasound Contrast Imaging, Jan. 26-27, 2006.

Frinking, P.J.A. et al "Ultrasound Contrast Imaging: Current and New Potential methods" Ultrasound in Medicine and Biology, New York, New York, US, vol. 26, No. 6, Jul. 2000, pp. 965-975.

Vos et al., Repetition Rate Imaging of Bubbles, Abstract of the Eleventh European Symposium on Ultrasound Contrast Imaging, Rotterdam, The Netherlands, Jan. 26-27, 2006.

* cited by examiner

PULSE INVERSION SEQUENCES FOR NONLINEAR IMAGING

RELATED APPLICATIONS

This application claims priority to U.S. Provisional Application Ser. No. 60/821,106, filed Aug. 1, 2006, and U.S. Provisional Application Ser. No. 60/824,862, filed Sep. 7, 2006, both of which are fully incorporated hereby by reference.

FIELD OF THE INVENTION

The present invention relates to pulse inversion sequences for nonlinear tissue imaging and microbubble imaging.

BACKGROUND INFORMATION

Intravascular ultrasound (IVUS) is an established tool for obtaining ultrasound images within the vascular system. IVUS is a method by which a catheter-based high frequency (e.g., 20 to 50 MHz) transducer is used to create high resolution images of the lumen and vascular wall of larger vessels. It is an established interventional cardiology tool for gaining insight into the size, structure, and composition of atherosclerotic plaque located within coronary arteries.

FIG. 1 shows an exemplary IVUS catheter within a body lumen. The IVUS catheter comprises a transducer at its distal end for obtaining ultrasound images from within the body lumen. The transducer may be comprised of a single element transducer that mechanically scans to create a cross-sectional image, e.g., by rotating the transducer with a drive shaft and having the transducer transmit pulses as it rotates. Current high frequency imaging systems employ a mechanically scanned single element transducer and single pulse per line image formation Ultrasound images may also be obtained using an array of transducer elements that electronically scans an image. Three-dimensional (3D) imaging may be performed using a two-dimensional (2D) imaging array by mechanically moving the 2D imaging array to obtain 2D images at different positions and combining the 2D images to form a 3D image. 3D images may also be obtained using a single transducer element. This may be done by rotating the transducer to obtain 2D images, moving the transducer laterally (e.g., pulling back the transducer) to obtain 2D images at different locations, and combining the 2D images to form a 3D image.

Nonlinear tissue imaging techniques have also been developed. In this case, nonlinear propagation of an ultrasound pulse through tissue within the body (increasing with transmit pressure) gives rise to harmonics of the transmit frequency (centered at approximately positive integer multiples of the transmit frequencies). A nonlinear imaging system generates ultrasound images using the nonlinear echoes arising from nonlinear interactions of the transmitted ultrasound pulses with tissue. The nonlinear echoes may be second harmonic (twice the transmit frequency), or combinations of second and higher order harmonics, referred to as superharmonic imaging, as described by Ayache Bouakaz et al., "Native tissue imaging at superharmonic frequencies," IEEE Trans Ultrason Ferroelec Freq Control, Vol. 50, No. 5, pp. 496-506, 2003, which is incorporated herein by reference. The formation of nonlinear tissue images can result in a reduction of imaging artifacts and thereby improve image quality. Nonlinear imaging requires isolation of the nonlinear echoes by suppressing the fundamental frequency (i.e., transmit frequency). The fundamental frequency may be suppressed using a pulse inversion (PI) technique, bandpass filtering, or a combination of these approaches. The basic PI technique, as described by David H. Hope Simpson et al., "Pulse inversion doppler: A new method for detecting nonlinear echoes from microbubble contrast agents," IEEE Trans Ultrason Ferroelec Freq Control, Vol. 46, No. 2, pp. 372-382, 1999, which is incorporated herein by reference, involves transmitting a pulse and its inverted counterpart along each scan line to cancel out the fundamental signal. A primary advantage of this approach is that it does not require separate frequency bands for the fundamental and harmonic signals, and thereby permits the use of wider bandwidth transmit signals, which can potentially overlap with the nonlinear signals. Wide bandwidth transmit signals in turn improve the axial resolution of the imaging system.

An application of IVUS tissue harmonic imaging is to improve the image quality of atherosclerotic plaque imaging, which may in turn improve diagnosis, treatment planning and therapeutic monitoring. Image artifacts that may be improved with such an approach are catheter sheath artifacts, stent reverberation artifacts, and the presence of calcification within plaques.

Ultrasound contrast imaging employs a contrast agent to enhance the detection and imaging of blood flow or blood vessels within the body. The contrast agent may be comprised of echogenic microbubbles having ultrasound scattering properties that are distinct from those of tissue, thereby enhancing contrast between sites containing the microbubbles and surrounding tissue. Microbubbles are encapsulated gas bubbles of diameters small enough to pass through the capillary beds (typically <10-12 microns) dispersed in an aqueous medium, and may be injected into the blood stream in order to enhance detection of blood vessels (e.g., microvessels) at the imaging location. Typically contrast agents are designed to contain substantial numbers of bubbles of a size that is resonant, or acoustically active at diagnostic ultrasound frequencies (2-10 microns in diameter). These bubbles may have bubbles below 2 microns present, or below 1 micron present. Bubbles can be made to have most bubbles on the order of 1-2 microns in diameter and below. Microbubbles are encapsulated with either a stiff shell or stabilized with a surfactant shell that is compliant (e.g., lipids, albumin). This shell can affect the mechanical properties of bubbles. Microbubbles may also be employed to target (i.e. attach through interaction between molecules within or attached to the microbubble shell and molecular epitopes of interest expressed by tissue within the body) molecules of interest within the body. This may be achieved by introducing these bubbles into the body and allowing their accumulation at a sight of interest and then imaging them. Microbubbles can be induced to exhibit scattering properties that are different from those of tissue. For example, microbubbles can emit second harmonic signals (at different pressure levels than those required to generate tissue harmonics), superharmonic signals, subharmonic signals (particularly but not exclusively centered near at ½ the transmit frequency), ultraharmonic signals (particularly but not exclusively at 1.5, 2.5, 3.5 etc of the transmit frequency. Microbubbles can be destroyed, thereby enabling the implementation of indicator dilution techniques. During destruction, broadband acoustic emissions can be made, and interpulse decorrelation can occur. Transient bubble behavior, sensitive to pulse frequency shape and phase, can also be stimulated. Microbubbles are more acoustically active in the vicinity of their resonant frequencies, though advantageous emissions can be induced when transmitting below the resonant frequency (e.g., second harmonic or destruction) or above (e.g., subharmonics). Bubble resonant frequencies are higher for smaller bubbles. In IVUS frequency ranges nonlinear activity of bubbles has been detected in bubbles on the order of 2 microns and below.

All of the above behaviors, and others can be used either alone or in combination to improve the detection of microbubbles in the presence of tissue for the purposes of improved blood compartment or molecular detection. Examples of microbubbles are disclosed in WO 2006/015876, WO 97/29783, WO 2004/0069284, U.S. Pat. No. 5,271,928, U.S. Pat. No. 5,445,813, U.S. Pat. No. 5,413,774, U.S. Pat. No. 5,597,549, U.S. Pat. No. 5,827,504, U.S. Pat. No. 5,711,933, and U.S. Pat. No. 6,333,021, all of which are incorporated herein by reference.

One application of IVUS contrast imaging is in the detection, visualization and quantification of vasa vasorum in or surrounding atherosclerotic plaques. This would be done for the purposes of diagnosis, treatment planning and therapeutic monitoring. This would be achieved by applying bubble detection procedures following either the local or systemic injection of untargeted contrast agent. The vasa vasorum are microvessels surrounding and penetrating the walls of larger blood vessels. While their precise role is not entirely understood, evidence is mounting that the growth of neovascular vasa vasorum through the process of angiogenesis is a crucial step in the development of atherosclerotic plaques. This realization has led to an emerging interest in the vasa vasorum as a therapeutic target and a growing demand for vasa vasorum imaging techniques. These techniques could also be used in conjunction with tissue structure information provided by IVUS. For example to determine the location of vascularity relative to plaque structure, potentially useful information. In addition to untargeted agent, targeted contrast agents are also considered for this application. For example, targeting to neovascular endothelial cell markers. Agent could also be targeted to other molecules of interest in atherosclerosis.

Recently, the feasibility of performing both second harmonic and wide bandwidth subharmonic contrast imaging with an IVUS system operating at high frequencies has been demonstrated by David E. Goertz et al., "Nonlinear Intravascular Ultrasound Contrast Imaging," Ultrasound in Med & Biol., Vol. 32, No. 4, pp. 491-502, 2006, which is incorporated herein by reference. These nonlinear contrast imaging approaches provide a promising means for improving vessel lumen boundary detection and IVUS vasa vasorum imaging.

As discussed above, in nonlinear imaging applications, it is important to achieve effective suppression of the fundamental signal. The basic pulse inversion (PI) technique its widely used for fundamental suppression. However, the effectiveness of the basic PI technique is reduced by transducer motion and the relative motion between the transducer and tissue, which cause the fundamental echoes arising from a transmitted pulse and its inverted counterpart to not cancel out completely. The reduction in the effectiveness of the PI technique was demonstrated for a mechanically rotating transducer of an IVUS catheter by Martin E. Frijlink et al. "A simulation Study on Tissue Harmonic Imaging with a Single-element Intravascular Ultrasound Catheter," J. Acoust. Soc. Am., Vol. 120, No. 3, September 2006, which is incorporated herein by reference.

Because mechanical scanning requires moving the transducer, nonlinear imaging systems using mechanical scanned transducers suffer greater degradation in fundamental frequency suppression due to motion effects compared with array-based imaging system where the transducers are normally stationary and electrically scanned. 3D imaging using a 2D array-based system also suffers degradation in fundamental frequency suppression due to motion effects because the array has to be mechanically moved to obtain 2D images at different positions to form the 3D image.

Therefore, there is a need to improve fundamental frequency suppression for nonlinear imaging systems using mechanically scanned transducers.

Many nonlinear imaging approaches would benefit from improved fundamental frequency suppression. For example, the nonlinear ultrasound contrast imaging approaches discussed above would benefit from improved fundamental frequency suppression. Examples of other imaging approaches that may benefit from improved fundamental frequency suppression include, but are not limited to:

1. Broadband signals from bubble disruption. Fundamental suppression is key for discriminating broadband contrast signals from tissue signals.

2. 'Pulse-inversion fundamental' techniques, which take advantage of energy in the transmit frequency range, which can be present for a number of reasons (e.g., broadening of the fundamental frequency response, asymmetric bubble responses to compressional and rarefactional cycles). A pulse-inversion-based fundamental imaging technique has been described by Che-Chou Shen and Pai-Chi Li, "Pulse-inversion-based fundamental imaging for contrast detection," IEEE Trans Ultrason Ferroelec Freq Control, Vol. 50, No. 9, pp. 1124-1133, 2003, which is incorporated herein by reference. Transducer motion reduces the ability to use Fundamental frequency energy originating from bubble vibrations or reflections.

3. Dual frequency approaches, whereby a low frequency signal modulates the high frequency scattering response from bubbles, as described in the patents WO 2005/071437A1 and WO 2006/001697A2, which are incorporated herein by reference. In this case bubbles are detected in the high frequency transmit bandwidth, using differences from the bubbles during low frequency compression and rarefaction cycles. A key to the success of this technique is to achieve the effective suppression of the tissue signal at high frequencies, through for example pulse inversion (or subtraction in post-processing) techniques, which can be corrupted by relative tissue and transducer motion.

4. 'Repetition rate imaging', where larger bubbles are stimulated to oscillate by sending high frequency ultrasound pulses at a pulse repetition frequency (PRF) at or near the bubble resonant frequencies, as described by Hendrik J. Vos et al., "Repetition rate imaging of bubbles", abstract of the Eleventh European Symposium on Ultrasound Contrast Imaging, Rotterdam, the Netherlands, Jan. 26-27, 2006, which is incorporated herein by reference. Differences between oscillating bubbles and tissue may then be detected with appropriate pulse inversion sequences, where fundamental frequency suppression may be critical in the success of this technique.

5. 'Bubble memory' techniques, which use the subtraction of pulses of different lengths to isolate tissue and bubble signals, based on the assumption that the acoustic response of tissue is 'memoryless', whereas bubbles have 'memory', as described in the patent WO 2006/021400A1, which is incorporated herein by reference. Optimized subtraction, reducing the effect of a moving transducer relative to the tissue and contrast, of pulses is key to the success of this technique.

6. Combinations of above mentioned techniques.

These imaging approaches suffer even more from poor fundamental frequency suppression.

SUMMARY

Provided herein are Pulse-Inversion (PI) sequences that provide for fundamental frequency suppression in nonlinear imaging applications. Examples of nonlinear imaging applications include second harmonic, subharmonic, and ultraharmonic contrast imaging. In an embodiment, a weighting scheme is applied to the received echo pulses resulting from transmit pulses of alternating polarity to reduce the effect of transducer motion. In an embodiment, a three-pulse weighting scheme is applied to a PI sequence. In other embodiments, different combinations of the three-pulse weighting scheme are applied to a PI sequence.

DETAILED DESCRIPTION

Figure 1:
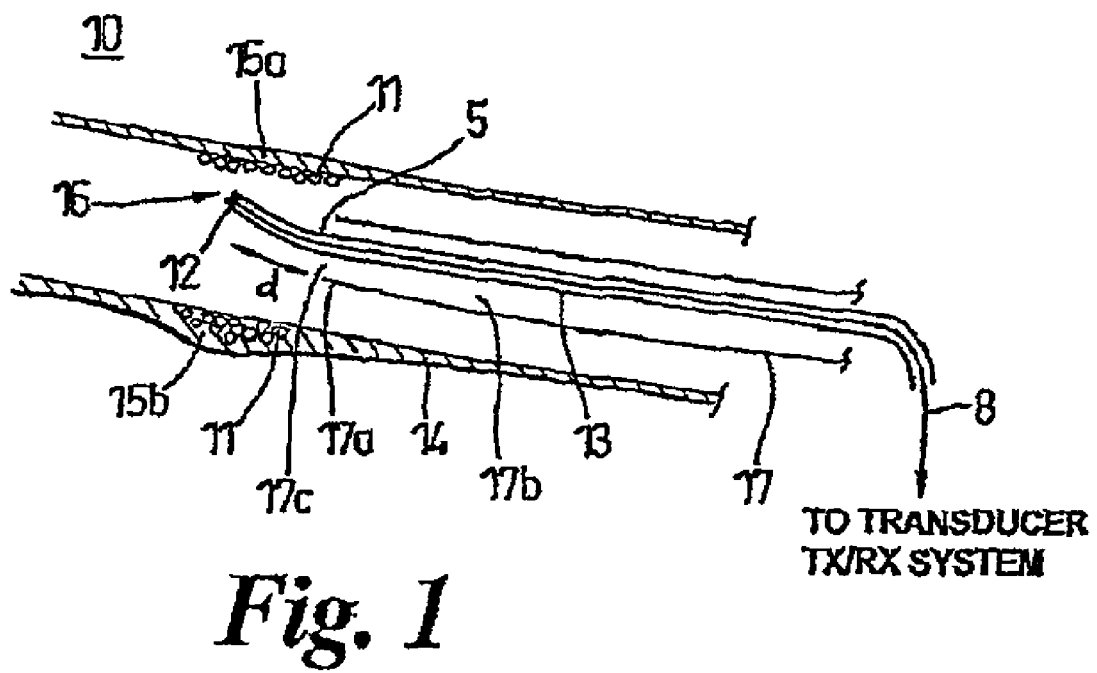
FIG. 1 shows an exemplary IVUS catheter with a transducer at its distal end.

Provided herein are PI-sequences that achieve significant improvements on the fundamental suppression (of both tissue and contrast) for nonlinear image acquisitions, e.g., with a mechanically scanned transducer. These nonlinear acquisitions may include subharmonic, second harmonic, fundamental PI and dual-frequency-exposure acquisitions.

The PI-technique according to the invention applies weighting schemes for processing the received echoes from transmit pulses of alternating polarity to reduce the effect of transducer motion based on the assumption that optimal cancellation of one pulse is achieved by adding the average of two adjacent pulses of opposite polarity.

In an embodiment, the PI-technique applies a weighting scheme that results in a basic 3-pulse sequence of $[P_1^- + 2 \cdot P_2^+ + P_3^-]$, where $[P^+]$ is the response from a positive polarity pulse and $[P^-]$ the response of a negative (opposite) polarity pulse. Linear combinations of this basic 3-pulse sequence can be described by the following first generalization:

$$\sum_{t=1}^{n} P_t^{+/-} + 2 \cdot P_{t+1}^{-/+} + P_{t+2}^{+/-} \qquad 1.$$

for $n = 1, 2, 3, 4, 5, 6, 7, \ldots$ where t and t+1 indicate neighboring pulse responses. This results in multi-pulse sequences with the following weightfactors:

1-2-1
1-3-3-1
1-3-4-3-1
1-3-4-4-3-1
1-3-4-4-4-3-1
1-3-4-...-4-3-1

Linear combinations of the basic 3-pulse sequence can also be described by the following second generalization:

$$\sum_{t=1}^{n} P_t^{+/-} + 2 \cdot P_{t+1}^{-/+} + P_{t+2}^{+/-} \qquad 2.$$

for $n = 1, 3, 5, 7, 9, 11, \ldots$ where the index of summation t is increment by two instead of one, as in the first generalization. This results in multi-pulse sequences with the following weightfactors:

1-2-1
1-2-2-2-1
1-2-2-2-2-2-1
1-2-2-...-2-2-1

As with tissue second harmonic imaging, the use of the described Pulse-Inversion Sequences will also be beneficial for second harmonic, subharmonic and ultraharmonic microbubble imaging. In these circumstances the center frequency of the nonlinear frequency bands are separate from the transmit separate frequency; however, for wider bandwidth signals (beneficial for improved axial resolution) there may be considerable overlap in the frequency content of these bands. A more effective cancellation of the fundamental frequency tissue signals will again reduce the requirement of real-time bandpass filtering and enable the inclusion of more contrast signal bandwidth. The latter point is particularly significant since the harmonic and subharmonic signals are broadened by the bubble response, even in the absence of microbubble disruption.

The use of the Pulse-Inversion Sequences in the context of contrast imaging may be particularly useful when employing bubble detection techniques that do not rely upon the use of separate frequency bands for the separation of contrast and tissue signals. In this case residual tissue signals from tissue motion will severely degrade the contrast to tissue ratios. Techniques that would also benefit from the inventive Pulse-Inversion Sequences to enhance fundamental suppression include, but are not limited to: broadband bubble destruction imaging, fundamental frequency imaging, dual frequency imaging, repetition rate imaging, and bubble memory imaging techniques, techniques which have been described in more detail in the background section.

The Pulse-Inversion Sequences may be used in these contrast detection techniques by applying the proposed weighting schemes for processing the received echoes from transmit pulses of alternating polarity. For optimal use, it may be beneficial for some contrast imaging techniques to replace the transmit sequence (e.g., changing the order of the transmit pulses, adding transmit pulses, etc.).

Initial simulations suggest that the beam shape can have its effect on the pulse weighting if more than 3 receive pulses are combined. The beam shape might be used to weight the basic weighting scheme [−1 2 −1], which subsequently may be dependent on the depth.

A specific example of a high-frequency application with a mechanically-scanned transducer is harmonic IVUS with a continuously-rotating single-element. For this example, initial simulations were performed.

Simulations

A simulation tool was developed to calculate nonlinear high-frequency beams in tissue-mimicking media and to investigate the influence of transducer rotation on the efficiency of the weighted PI-signal processing. In this example, 20 MHz Gaussian pulses (2 MPa, 50% bandwidth) were propagated through a scattering and attenuating (1.0 dB×cm−1×MHz−1) medium, resulting in the generation of second harmonic signal at 40 MHz. Fundamental suppression was investigated for a range of inter-pulse angles (0.15°−1.5°) for different PI-sequences. The inter-pulse angle of 0.15° corresponds to the angle as used in initial harmonic IVUS experiments as performed with a prototype system using a line-density of 2400 lines per rotation. The inter-pulse angle of 1.5° corresponds to an angle with a line density of 256 lines per rotation.

FIG. 1 shows the effects of different PI-sequences as compared to no Pulse-Inversion and to basic PI using $[P_1^- + P_2^+]$, for an inter-pulse angle of 0.15°.

The average fundamental reduction between 18 and 22 MHz as compared to a single RF-trace is given in the table below:

| Sequence | Average reduction between 18-22 MHz | Extra reduction vs. basic PI |
|---|---|---|
| [1 1] (basic PI) | 28.2 dB | 0 dB |
| [1 2 1] | 34.8 dB | 6.6 dB |
| [1 2 2 2 2 2 1] | 38.8 dB | 10.6 dB |
| [1 3 4 4 4 3 1] | 38.5 dB | 10.3 dB |

Figure 2:
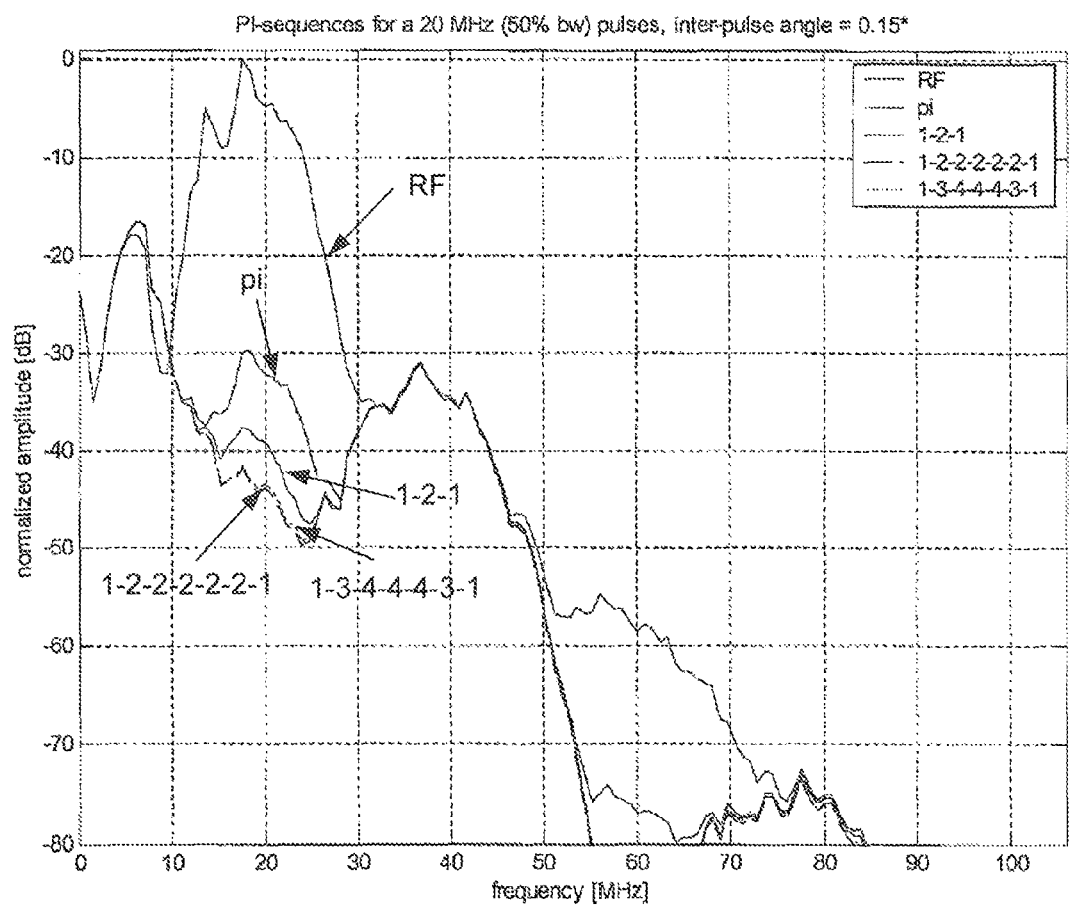
FIG. 2 is a graph showing the effects of different PI-sequences as compared to no PI and basic PI for an inter-pulse angle of 0.15°.
Figure 3:
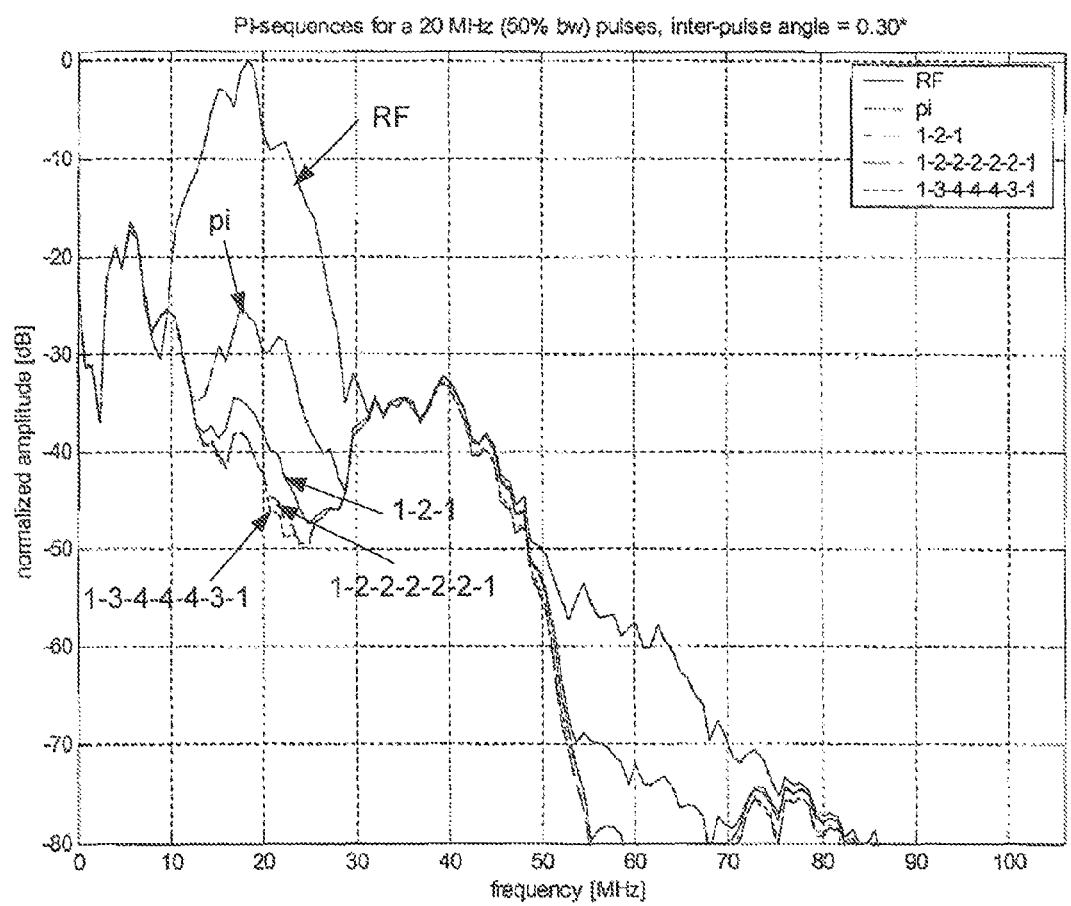
FIG. 3 is a graph showing the effects of different PI-sequences as compared to no PI and basic PI for an inter-pulse angle of 0.30°.

The same has been simulated for an inter-pulse angle of 0.30°. FIG. 2 shows the effects of different PI-sequences as compared to no Pulse-Inversion and to basic PI using $[P_1^- + P_2^+]$, for an inter-pulse angle of 0.30°.

The average fundamental reduction between 18 and 22 MHz as compared to a single RF-trace is given in the table below:

| Sequence | Average reduction between 18-22 MHz | Extra reduction vs basic PI |
|---|---|---|
| [1 1] (basic PI) | 23.0 dB | 0 dB |
| [1 2 1] | 32.3 dB | 9.3 dB |
| [1 2 2 2 2 2 1] | 35.9 dB | 12.9 dB |
| [1 3 4 4 4 3 1] | 36.5 dB | 13.5 dB |

The graphs in FIGS. 1 and 2 only show the result of three of the proposed PI-sequences. Also, different interpulse angles will result in different effects of the proposed PI-sequences.

A 3-pulse PI-sequence [1 2 1] was also applied on RF-data from IVUS THI acquisitions (inter-pulse angle 0.15°) in rabbit aortas in vivo. The 3-pulse sequence improved the fundamental suppression by >6 dB.

Therefore, the effective application of weighted PI-sequences to reduce the effects of transducer rotation on fundamental frequency suppression has been shown. The weighted PI-sequences will help reduce relative tissue/transducer motion effects, leading to improved image quality in nonlinear tissue and contrast imaging. The weighted PI-sequences are ideally suited for fast real-time implementation, thereby reducing the requirements for relatively time-consuming digital bandpass filtering.

While embodiments of the present invention has been shown and described, various modifications may be made without departing from the scope of the present invention, and all such modifications and equivalents are intended to be covered.

REFERENCES

[1] Bouakaz A, de Jong N, Native tissue imaging at superharmonic frequencies, IEEE Trans Ultrason Ferroelec Freq Control 2003, 50 (5): 496-506.
[2] Hope Simpson D H, Chin C T, Burns P N, Pulse inversion doppler: A new method for detecting nonlinear echoes from microbubble contrast agents, IEEE Trans Ultrason Ferroelec Freq Control 1999, 46 (2): 372-382.
[3] Goertz D E, Frijlink M E, de Jong N, van der Steen A F W, Nonlinear intravascular ultrasound contrast imaging, Ultrasound Med Biol 2006, 32(4): 491-502.

What is claimed is:

1. A method for non-linear ultrasound imaging of a patient's body, comprising:

transmitting ultrasound excitation pulses of alternating polarity into the patient's body;
receiving ultrasound echo signals in response to the excitation pulses; and
applying a weighting scheme to the received ultrasound echo signals, wherein the weighting scheme is given by $$\sum_{t=1}^{n} a \cdot P_t^{+/-} + b \cdot P_{t+1}^{-/+} + c \cdot P_{t+2}^{+/-}$$

where t is an index of summation incremented by 1, t and t+1 indicate neighboring pulse responses, $P^{+/-}$ and $P^{-/+}$ are echo signals in response to excitation pulses of opposite polarities, n is an upper bound of summation and n is 3 or larger, and a, b, and c equal 1, 2, and 1, respectively.

2. The method of claim 1, wherein the received echo signals include harmonic responses.

3. The method of claim 1, wherein the received echo signals include subharmonic responses.

4. The method of claim 1, wherein the received echo signals include ultraharmonic responses.

5. The method of claim 1, further comprising:
introducing a catheter-based ultrasound transducer into the patient's body at a site of interest; and
mechanically scanning the transducer to image the site of interest.

6. The method of claim 5, wherein the site of interest is an artery.

7. The method of claim 5, further comprising introducing a contrast agent into the patient's body, wherein the excitation pulses interact differently with tissue and the contrast agent.

8. The method of claim 7, wherein the contrast agent is injected is injected into the patient's body in the vicinity of the transducer.

9. The method of claim 7, wherein the contrast agent is located in vasa vasorum.

10. The method of claim 7, wherein the excitation pulses are transmitted at a center frequency of 15 MHz or greater.

11. The method of claim 7, wherein the excitation pulses are transmitted at a center frequency of 20 MHz or greater.

12. The method of claim 5, wherein mechanically scanning the transducer comprises rotating the transducer.

13. The method of claim 5, wherein the transducer comprises a transducer array, the method further comprising:
mechanically moving the transducer array;
obtaining multiple two-dimensional images with the transducer array as the transducer array is moved; and
combining the multiple two-dimensional images to form a three-dimensional image.

14. The method of claim 5, wherein the transducer comprises a single transducer element, the method further comprising:
mechanically moving the single transducer element;
obtaining multiple two-dimensional images with the single transducer element as the single transducer element is moved; and
combining the multiple two-dimensional images to form a three-dimensional image.

15. The method of claim 1, further comprising introducing a contrast agent into the patient's body, wherein the excitation pulses interact differently with tissue and the contrast agent.

16. The method of claim 15, wherein the contrast agent comprises microbubbles.

17. The method of claim 16, further comprising imaging within the patient's body using a bubble disruption imaging technique.

18. The method of claim 16, further comprising imaging within the patient's body using a dual frequency imaging technique.

19. The method of claim 16, further comprising imaging within the patient's body using a repetition rate imaging technique.

20. The method of claim 16, further comprising imaging within the patient's body using a bubble memory imaging technique.

21. The method of claim 16, further comprising imaging within the patient's body using a bubble disruption imaging technique, a dual frequency imaging technique, a repetition rate imaging technique, a bubble memory imaging technique, or a combination thereof.

22. The method of claim 15, wherein the contrast agent is adapted to selectively locate at sites, or in regions, of specific character.

23. The method of claim 15, wherein the contrast agent is untargeted.

24. The method of claim 15, wherein the contrast agent is injected into the patient's body in the vicinity of the transducer.

25. The method of claim 15, wherein the contrast agent is injected into the patient's body at a location away from the transducer.

26. A method for non-linear ultrasound imaging within a patient's body, comprising:
   transmitting ultrasound excitation pulses of alternating polarity into the patient's body;
   receiving ultrasound echo signals in response to the excitation signals pulses; and
   applying a weighting scheme to the received ultrasound echo signals, wherein the weighting scheme is given by $$\sum_{t=1}^{n} a \cdot P_t^{+/-} + b \cdot P_{t+1}^{-/+} + c \cdot P_{t+2}^{+/-}$$

where t is an index of summation incremented by 2, t and t+1 indicate neighboring pulse responses, $P^{+/-}$ and $P^{-/+}$ are echo signals in response to excitation pulses of opposite polarities, n is an upper bound of summation and n is 2 or larger, and a, b, and c equal 1, 2, and 1, respectively.

27. The method of claim 26, wherein the received echo signals include harmonic responses.

28. The method of claim 26, wherein the received echo signals include subharmonic responses.

29. The method of claim 26, wherein the received echo signals include ultraharmonic responses.

30. The method of claim 26, further comprising:
   introducing a catheter-based ultrasound transducer into the patient's body at a site of interest; and
   mechanically scanning the transducer to image the site of interest.

31. The method of claim 30, wherein the site of interest is an artery.

32. The method of claim 30, further comprising introducing a contrast agent into the patient's body, wherein the excitation pulses interact differently with tissue and the contrast agent.

33. The method of claim 32, wherein the contrast agent is injected is injected into the patient's body in the vicinity of the transducer.

34. The method of claim 32, wherein the contrast agent is located in vasa vasorum.

35. The method of claim 32, wherein the excitation pulses are transmitted at a center frequency of 15 MHz or greater.

36. The method of claim 32, wherein the excitation pulses are transmitted at a center frequency of 20 MHz or greater.

37. The method of claim 30, wherein the transducer comprises a transducer array, the method further comprising:
   mechanically moving the transducer array;
   obtaining multiple two-dimensional images with the transducer array as the transducer array is moved; and
   combining the multiple two-dimensional images to form a three-dimensional image.

38. The method of claim 30, wherein the transducer comprises a single transducer element, the method further comprising:
   mechanically moving the single transducer element;
   obtaining multiple two-dimensional images with the single transducer element as the single transducer element is moved; and
   combining the multiple two-dimensional images to form a three-dimensional image.

39. The method of claim 30, wherein mechanically scanning the transducer comprises rotating the transducer.

40. The method of claim 26, further comprising introducing a contrast agent into the patient's body, wherein the excitation pulses interact differently with tissue and the contrast agent.

41. The method of claim 40, wherein the contrast agent comprises microbubbles.

42. The method of claim 41, further comprising imaging within the patient's body using a bubble disruption imaging technique.

43. The method of claim 41, further comprising imaging within the patient's body using a dual frequency imaging technique.

44. The method of claim 41, further comprising imaging within the patient's body using a repetition rate imaging technique.

45. The method of claim 41, further comprising imaging within the patient's body using a bubble memory imaging technique.

46. The method of claim 41, further comprising imaging within the patient's body using a bubble disruption imaging technique, a dual frequency imaging technique, a repetition rate imaging technique, a bubble memory imaging technique, or a combination thereof.

47. The method of claim 40, wherein the contrast agent is adapted to selectively locate at sites, or in regions, of specific character.

48. The method of claim 40, wherein the contrast agent is untargeted.

49. The method of claim 40, wherein the contrast agent is injected into the patient's body in the vicinity of the transducer.

50. The method of claim 40, wherein the contrast agent is injected into the patient's body at a location away from the transducer.

* * * * *